United States Patent
Taylor et al.

(10) Patent No.: US 10,486,116 B1
(45) Date of Patent: Nov. 26, 2019

(54) CONTINUOUS EXTRUSION SYSTEM

(71) Applicants: Graham Jeffrey Taylor, Knoxville, TN (US); Nima Tamaddoni Jahromi, Knoxville, TN (US)

(72) Inventors: Graham Jeffrey Taylor, Knoxville, TN (US); Nima Tamaddoni Jahromi, Knoxville, TN (US)

(*) Notice: Subject to any disclaimer, the term of this patent is extended or adjusted under 35 U.S.C. 154(b) by 130 days.

(21) Appl. No.: 15/846,136

(22) Filed: Dec. 18, 2017

(51) Int. Cl.
*B01F 3/08* (2006.01)
*A61K 9/127* (2006.01)

(52) U.S. Cl.
CPC .......... *B01F 3/088* (2013.01); *B01F 3/0803* (2013.01); *B01F 3/0865* (2013.01); *A61K 9/1277* (2013.01)

(58) Field of Classification Search
CPC .................................................. B01F 3/0803
USPC .................. 366/176.3, 182.2, 182.4, 189
See application file for complete search history.

(56) References Cited

U.S. PATENT DOCUMENTS

| | | | | |
|---|---|---|---|---|
| 8,308,340 B2* | 11/2012 | Ferrante | ........... | A61B 17/00491 |
| | | | | 222/137 |
| 9,107,668 B2* | 8/2015 | Melsheimer | ..... | A61B 17/12022 |
| 9,604,184 B2* | 3/2017 | Gettings | ............... | B01F 5/0685 |
| 2008/0110831 A1* | 5/2008 | Tsai | ........................ | A61M 1/02 |
| | | | | 210/645 |

* cited by examiner

*Primary Examiner* — David L Sorkin
(74) *Attorney, Agent, or Firm* — Gulf Coast Intellectual Property Group

(57) ABSTRACT

An extrusion system that is operable to facilitate the extrusion of a solution through manipulation of a first syringe and a second syringe. The extrusion system includes a tubing network wherein the tubing network includes a first portion coupled to a first port of an extrusion cartridge and a second portion coupled to a second portion of an extrusion cartridge. The first portion of the tubing network includes an inlet line having an inlet valve coupled therewith and a first syringe. A purge line and purge line clamp are further included in the first portion. The second portion includes a second syringe, an exit line and an exit line clamp. The extrusion system utilizes reciprocating movements of the plungers of the first syringe and second syringe to facilitate the passing of the solution through the extrusion cartridge.

13 Claims, 2 Drawing Sheets

CONTINUOUS EXTRUSION SYSTEM

PRIORITY UNDER 35 U.S.C SECTION 119(e) & 37 C.F.R. SECTION 1.78

This nonprovisional application claims priority based upon the following prior United States Provisional Patent Application entitled: Apparatus and Method of Use for Continuous Extrusion of Liposomes, Polymerosomes, Cells and Cellular Products and Nano or Micro-Scale Colloids, Application No.: 62/438,703 filed Dec. 23, 2016, in the name of Graham Jeffrey Taylor, which is hereby incorporated by reference for all purposes.

FIELD OF THE INVENTION

The present invention relates generally to extrusion apparatus, more specifically but not by way of limitation, a system that is configured to provide continuous extrusion of solutions containing lipids, copolymers or monomeric compounds that self-assemble into nano or microscale colloidal structures wherein the system provides scalability to large volumes and wherein the solution being extruded is contacted preferably by but not limited to single-use components.

BACKGROUND

Lipids are the building blocks of cell membranes. Scientists are continually finding new ways to use lipid-based constructs in applications, such as but not limited to drug delivery and gene transfection. In scientific studies lipids are used as materials for constructing model lipid bilayers (planar bilayers, giant unilamellar vesicles, large and small unilamellar vesicles) and other lipid-based constructs such as but not limited to nanodiscs, and nanocarriers. Other lipid-like molecules, membrane components, and even synthetic molecules are used in the creation of vesicles and self-assembled aggregates in solution. Such molecules may be charged or uncharged and include lipids as well as cholesterol, signaling lipids, lipid A, cardiolipin, proteins, surfactants, cell-derived lipids and molecules, and amphiphilic polymers and copolymers among other species. Often, lipids or similar amphiphiles are dissolved in an aqueous medium, such as but not limited to buffered water, and are further processed to produce unilamellar vesicles (UV) or liposomes. When the lipids or amphiphiles are initially dissolved, their amphiphilic structure drives self-assembly into sheets such that the hydrophobic lipid tails are not exposed to the surrounding water medium. Most commonly, the resulting structures are multilamellar vesicles (MLVs), or layered onion-like spheres (vesicles/liposomes) where each layer is comprised of the self-assembled lipids or amphiphiles. MLVs may also be formed by injecting organic solvent containing amphiphiles into aqueous solution. For many applications, MLVs are further processed to produce smaller unilamellar vesicles (SUVs) or liposomes by extrusion through a membrane with pores of specific diameter (typically 100-500 nm diameter). Extrusion is the most common method of processing and preparing liposomes.

In addition to extrusion, there are other established methods for sizing liposomes including emulsification, homogenization, microfluidization, organic-solvent injection, reverse phase evaporation, or sonication via a tip or bath style sonicator that delivers high energy to break up the MLVs into smaller UVs. Additionally, other novel techniques for liposome formation continues to emerge. The present invention specifically lies in the field of extrusion. In some cases, the lipids or amphiphiles may be dissolved in oil, placed in an oil-water emulsion, or placed in a double-emulsion or foam. The resulting colloidal structure may still be extruded to adjust their size and structure. Extrusion is also applicable for the sizing and processing of colloidal structures formed from polymers, copolymers, cells, cellular lipid extracts, cellular exosomes and liposomes and membrane "blebs", even cellular plasma membrane vesicles. Applications of extruded liposomes range from basic fundamental physical, chemical, and biological research to medical use as therapeutics, adjuvants, or delivery vehicles for drugs and small molecules, and also to cosmetic, agricultural, nutrition and nutraceutical, and food and beverage and dietary supplement industries.

There are existing devices that are used for extrusion, and these devices can be classified into categories: those intended for extrusion of small volumes (<1-10 mL) and those intended for extrusion of large volumes (from 1 mL up to 1 L, 10 L, or more). The present invention described herein can be used to extrude small or large volumes, but the present invention is specifically targeted towards at improving large-volume extrusion. Existing large-volume extrusion options are all similar, relying on high gas-pressure to drive liposome suspensions through a membrane with pores of defined and desired diameter. Examples of such currently available high-pressure extrusion systems include Lipex LiposoFast and Maximator systems. A deficiency with existing technology such as the aforementioned is the inability to precisely control the number of passes for a solution. Some systems only permit one extrusion per solution pass then require steps to initiate a second cycle or pass of the solution. As it is commonly required for many cycles or passes to achieve the required extrusion this can be time consuming. Additionally, existing technology a mixture of unextruded and extruded solution can be returned to the source container which leads to accuracy when determining a correct quantity of cycles and/or passes to extrude a solution.

Unlike existing devices and systems used for extrusion of small and large volumes of solution, the present invention disclosed herein can be used without having to "pour" or flow the suspension into any reusable part of the device that must be cleaned between uses. Avoidance of suspension contact with reusable parts is essential given that reusable parts are exposed to solutions and must thus be cleaned thoroughly, and possibly sterilized, i.e. for pharmaceutical or medical preparation or use, between production runs of different batches or lots of solutions. The need to clean, assemble, extrude, and clean again leads to a significant amount of lost time and cost in every single batch of extrusion. Utilization of these types of extruders leads to significant risk of contamination or carryover from sample to sample, despite the required rigorous cleaning procedures. Cleaning is particularly difficult if not impossible, often requiring harsh organic and environmentally unfriendly solvents like chloroform, ethanol, methanol, acetonitrile, or other solvents. Cleaning proves extremely difficult if cholesterol, proteins, membrane receptors and proteins, or other drugs, biomolecules, nanoparticles, and small molecules containing hydrophobic regions are used. In some cases, cleaning requires specialized harsh detergents and treatment, all of which increases cost and introduces significant risk of contamination. It is known in the art that the inherent risks associated with the need for cleaning which, even when done properly and according to manufacturer's recommendations, often fail to completely remove all material resulting in trace contaminants left behind. For applications in medical and pharmaceutical, food, cosmetic, and other industries, contamination due to improper cleaning and assembly could cause, infection physical harm to patients and even death, unwanted side effects, unintended consequences, blockage of capillaries and blood flow, and otherwise detrimental outcomes.

Accordingly, there is a need for continuous extrusion system that has no upper limit on the total volume that can be processed, controls the number of cycles and/or passes of a solution and further uses specially designed kits wherein the extrudant solution preferably comes into contact with only single-use, disposable components.

SUMMARY OF THE INVENTION

It is the object of the present invention to provide a continuous extrusion system that is provided in a pre-assembled kit and is operable to extrude solutions containing liposomes or similar colloids.

Another object of the present invention is to provide a continuous extrusion system that is configurable to utilize a single or reusable use liposome extrusion cartridge.

A further object of the present invention is to provide a continuous extrusion system configured to provide extrusion of a large volume range of solutions.

Still another object of the present invention is to provide a continuous extrusion system that is configured to provide extrusion of small and large volumes of solutions wherein the system of the present invention includes replaceable and sterilized components for the continuous extrusion system.

An additional object of the present invention is to provide a continuous extrusion system operable to extrude solutions containing liposomes or similar colloids that reduces and/or eliminates the need to clean the components thereof.

Yet a further object of the present invention is to provide a continuous extrusion system that is configured to provide extrusion of small and large volumes of solutions that includes alternate techniques and/or elements for driving fluid flow such as but not limited to high pressure gas, pneumatics, pumps such as but not limited to peristaltic pumps or mechanically driven elements such as but not limited to syringes.

Another object of the present invention is to provide a continuous extrusion system operable to extrude solutions containing liposomes or similar colloids wherein the system is configured to control the temperature of the solution during the entire extrusion process.

Still an additional object of the present invention is to provide a continuous extrusion system that is configured to provide extrusion of small and large volumes of solutions wherein the system includes a purge line and at least one fluid drive element.

To the accomplishment of the above and related objects the present invention may be embodied in the form illustrated in the accompanying drawings. Attention is called to the fact that the drawings are illustrative only. Variations are contemplated as being a part of the present invention, limited only by the scope of the claims.

BRIEF DESCRIPTION OF THE DRAWINGS

A more complete understanding of the present invention may be had by reference to the following Detailed Description and appended claims when taken in conjunction with the accompanying Drawings wherein:

DETAILED DESCRIPTION

Figure 1:
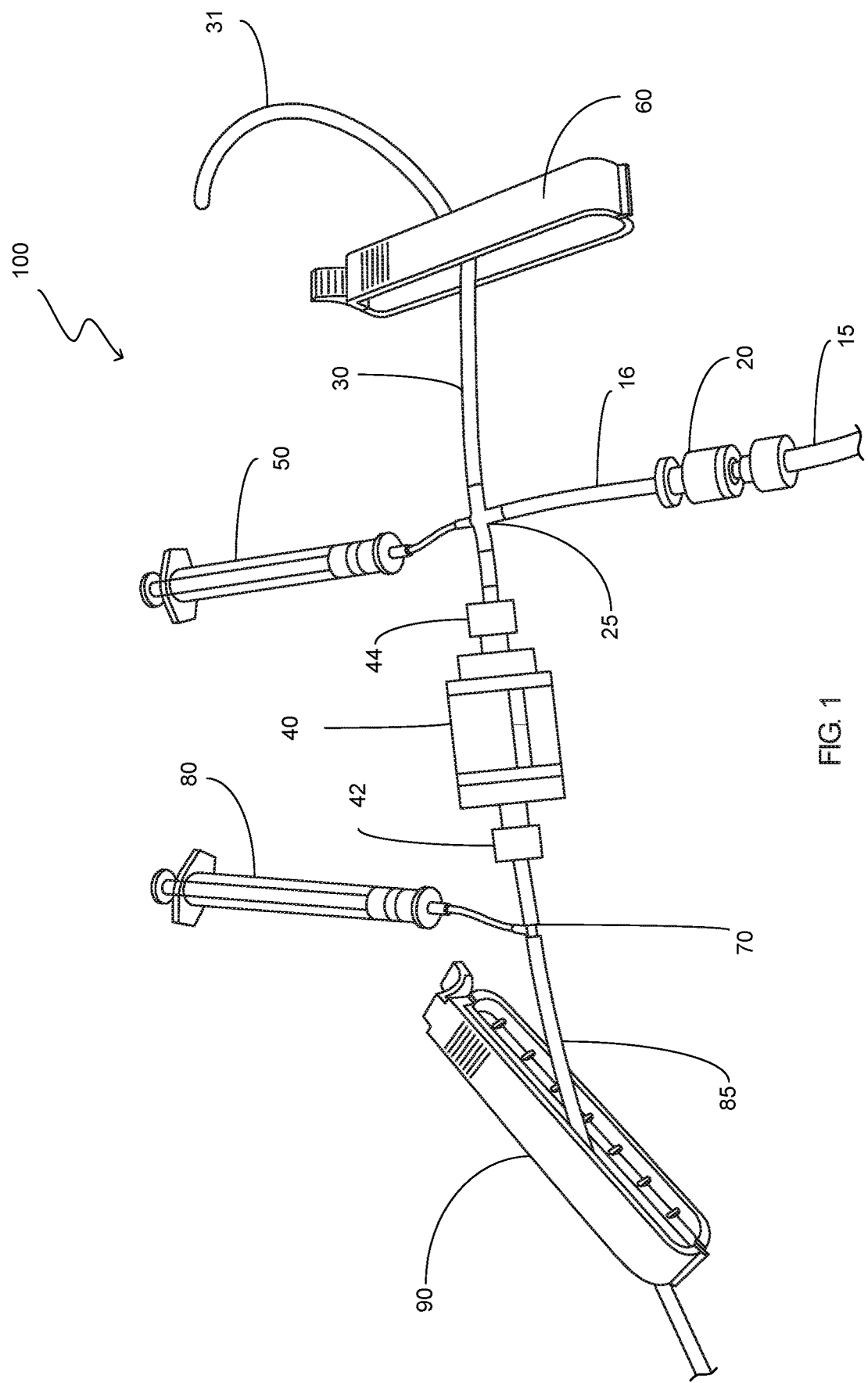
FIG. 1 is perspective view of an embodiment of the present invention.

Referring now to the drawings submitted herewith, wherein various elements depicted therein are not necessarily drawn to scale and wherein through the views and figures like elements are referenced with identical reference numerals, there is illustrated an continuous extrusion system 100 constructed according to the principles of the present invention.

An embodiment of the present invention is discussed herein with reference to the figures submitted herewith. Those skilled in the art will understand that the detailed description herein with respect to these figures is for explanatory purposes and that it is contemplated within the scope of the present invention that alternative embodiments are plausible. By way of example but not by way of limitation, those having skill in the art in light of the present teachings of the present invention will recognize a plurality of alternate and suitable approaches dependent upon the needs of the particular application to implement the functionality of any given detail described herein, beyond that of the particular implementation choices in the embodiment described herein. Various modifications and embodiments are within the scope of the present invention.

It is to be further understood that the present invention is not limited to the particular methodology, materials, uses and applications described herein, as these may vary. Furthermore, it is also to be understood that the terminology used herein is used for the purpose of describing particular embodiments only, and is not intended to limit the scope of the present invention. It must be noted that as used herein and in the claims, the singular forms "a", "an" and "the" include the plural reference unless the context clearly dictates otherwise. Thus, for example, a reference to "an element" is a reference to one or more elements and includes equivalents thereof known to those skilled in the art. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

References to "one embodiment", "an embodiment", "exemplary embodiments", and the like may indicate that the embodiment(s) of the invention so described may include a particular feature, structure or characteristic, but not every embodiment necessarily includes the particular feature, structure or characteristic.

Referring in particular to FIG. 1, an exemplary embodiment of the continuous extrusion system 100 is illustrated therein. The continuous extrusion system 100 includes a tubing network 10 that as will be further discussed herein is configured to direct fluid flow into, within and out of the the continuous extrusion system 100. The tubing network 10 is manufactured from a plurality of tubing line that is manufactured from a durable suitable material. It is contemplated within the scope of the present invention that the tubing line could additionally be sterilized for applications requiring such conditions. Inlet line 15 is operably coupled to a desired solution (not illustrated herein) and directs the solution into the inlet check valve 20. Inlet line 15 is sealably coupled to inlet check valve 20 wherein inlet check valve 20 is a one way valve configured to permit flow of solution into the tubing network. It is contemplated within the scope of the present invention that the inlet check valve 20 could be a manual valve or be controlled by a suitable electronic or electromechanical technique.

The second portion 16 of the inlet line 15 is intermediate the inlet check valve 20 and the union 25 and functions to operably couple the inlet check valve 20 to union 25. Union 25 is a four way union that provides operable connections with the purge line 30, extrusion cartridge 40 and the first syringe 50. The purge line 30 is intermediate the union 25 and purge line clamp 60. The purge line clamp 60 has a first position and a second position. In its first position the purge line clamp 60 is in an open position so as to allow fluid to exit the tubing network 10 in order to allow a user to purge the tubing network of air or another solution. In its second position the purge line clamp 60 is in a closed position so as to inhibit the flow of fluid therepast. It should be understood that the purge line clamp 60 illustrated herein is exemplary only and that it is contemplated within the scope of the present invention that the purge line clamp 60 could be either electronic or manual and be constructed using various styles of line clamps or similar elements such as but not limited to a valve, solenoid, pneumatically actuated pinch clamp, or other mechanical techniques. The purge line 30 includes a portion 31 opposite the purge line clamp 60 that is operably to allow air and/or fluid to egress from the tubing network 10 when the purge line clamp 60 is in its first position. Those skilled in the art will recognize that the portion 31 could extend various lengths so as to direct the fluid to a desired collection location.

Fluidly coupled to union 25 is first syringe 50. First syringe 50 is a conventional syringe and it is contemplated within the scope of the present invention that the first syringe 50 could be provided in numerous alternate volume sizes. The first syringe 50 as will be further discussed herein provides a driving means for moving fluid within the tubing network 10. It is contemplated within the scope of the present invention that the first syringe 50 could be controlled either manually or utilizing an automated means. Further it is contemplated within the scope of the present invention that alternate techniques for manipulating the fluid within the tubing network 10 could be utilized in place of and/or in conjunction with the first syringe 50. The first syringe 50 is fluidly coupled to union 25, which is fluidly coupled to extrusion cartridge 40. It is contemplated within the scope of the present invention that the extrusion cartridge 40 could be various sizes and types. The extrusion cartridge 40 includes opposing ports 41, 42 configured to facilitate the flow of fluid therethrough. While one extrusion cartridge 40 it is contemplated within the scope of the present invention that the continuous extrusion system 100 could have a tubing network 10 configured to accommodate more than one extrusion cartridge 40 in configurations such as but not limited to series, parallel or combination thereof.

Operably coupled to port 42 is second union 70. Second union 70 provides fluid coupling intermediate the second syringe 80 and the extrusion cartridge 40. The second syringe 80 is similar to first syringe 50 and is configured to provide a fluid driving means within the tubing network 10. As with the first syringe 50 the second syringe 80 could be either manual or controlled by an automated technique. The process of moving fluid within the tubing network 10 for the purpose of extrusion thereof will be further discussed herein. Union 70 is operably coupled to exit line 85. Exit line 85 has operably coupled thereto an exit line clamp 90. The exit line clamp 90 has a first position and a second position. In its first position the exit line clamp 90 is open so as to allow fluid to flow therepast and be directed towards a collection location. In its second position the exit line clamp 90 is in a closed position so as to prevent the flow of fluid therepast. It is contemplated within the scope of the present invention that the exit line clamp 90 could be either manual or electronic and be constructed using numerous types of clamping elements to include but not limited to valves.

Figure 2:
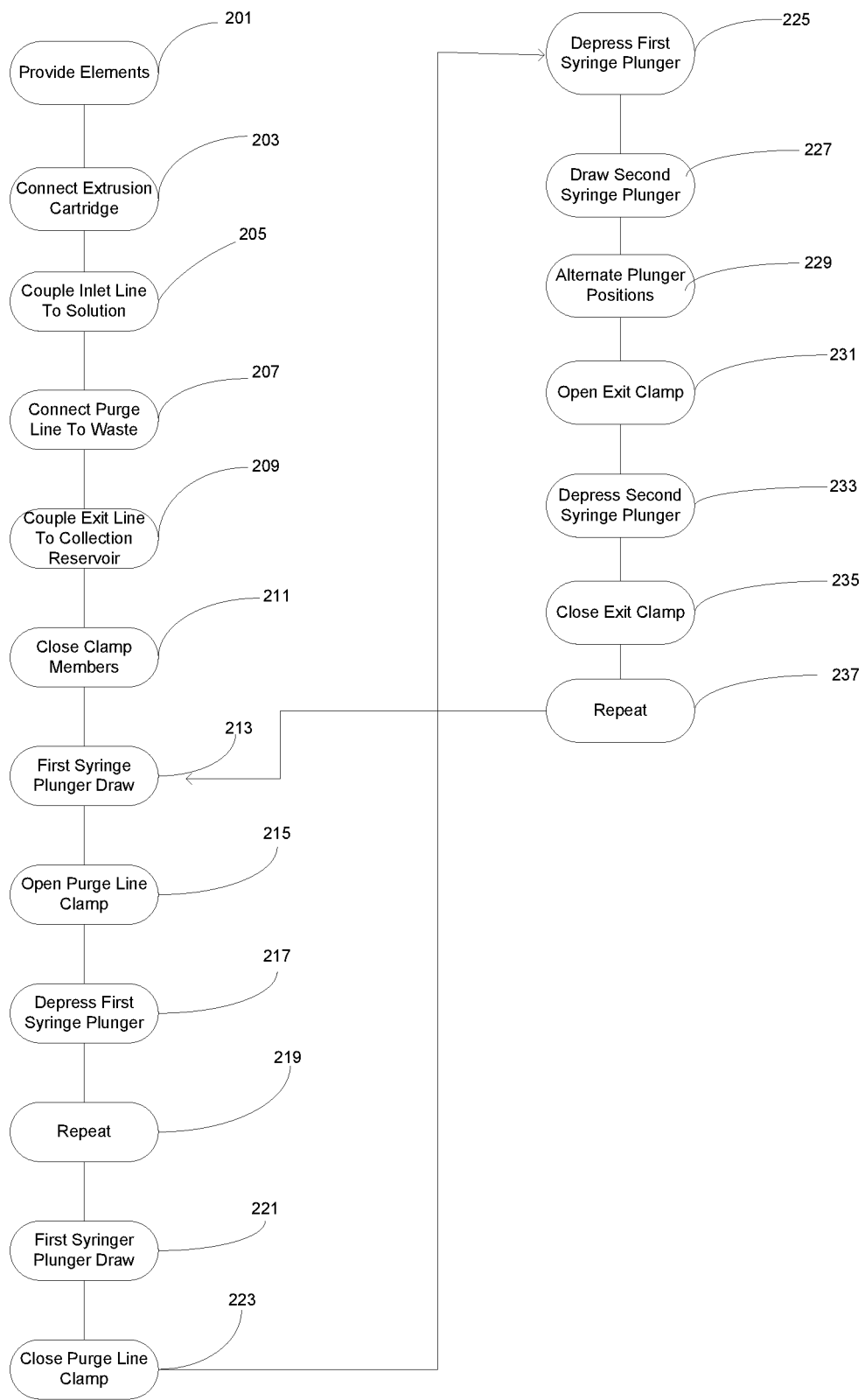
FIG. 2 is flowchart of the process of utilization of the system of the present invention.

Now referring to FIG. 2 herein, the method of the continuous extrusion system 100 is outlined therein. In step 201 the elements described herein are provided to a user. It is contemplated within the scope of the present invention that the elements of the invention could be provided in various pre-connected configurations. By way of example but not limitation, the inlet line 15, inlet check valve 20, union 25, purge line 30 and the first syringe 50 could be provided as a pre-connected configuration. Additionally, the second syringe 80, union 70 and exit line 85 could be provided in a pre-connected configuration. Providing pre-connected configurations as described herein allows a user to coupled the pre-connected configurations to a extrusion cartridge 40 and begin use of the continuous extrusion system 100. In step 203, the extrusion cartridge is operably coupled to the tubing network 10 via ports 41,42. Step 205, the inlet line 15 is fluidly coupled to a vessel having a solution therein that requires extrusion. In step 207, the portion 31 of the purge line 30 is operably coupled to a suitable waste reservoir or to a container containing the solution. Step 209, the exit line 85 is coupled to a suitable collection container. In step 211, the purge line clamp 60 and exit line clamp 90 are placed in their closed positions. Step 213, either manually or via automated technique, the plunger of the first syringe is drawn upward. It should be noted that prior to step 203, the plungers of the first syringe 50 and the second syringe 80 are in a fully depressed position. In step 215, the purge line clamp 60 is moved to its open position. Step 217, the plunger of the first syringe 50 is moved to its fully depressed position and the purge line clamp 60 is moved back to its closed position. In Step 219, step 213 through step 217 is repeated until a satisfactory amount of air has been removed. Step 221, the plunger of the first syringe 50 is drawn upward. In step 223, the purge line clamp 60 is in its closed position. Step 225, the plunger of the first syringe 50 is moved to its fully depressed position. In step 227, which simultaneously occurs with step 225, the plunger of the second syringe 80 is drawn upward at a rate identical to that of the movement of the plunger of the first syringe 50. In step 229, the plungers of the first syringe 50 and second syringe 80 are alternately moved intermediate fully depressed and drawn positions so as to pass the fluid contained therein through the extrusion cartridge 40. It should be understood that various application may require that the solution contained in the tubing network 10 only require one pass through the extrusion cartridge 40 or the solution could require multiple passes. In step 231, the exit line clamp 90 is moved to its open position. Step 233, the plunger of the second syringe 80 is moved to its fully depressed position. This movement of the plunger of the second syringe 80 evacuates the solution therefrom and the solution is directed through the exit line 85 into a suitable collection container. In step 235, the exit line clamp 90 is returned to its closed position. Step 237, if desired a user will return to step 213 and repeat steps 213 through step 235 in order to perform extrusion of a desired solution volume that may exceed the volume capacity of the first syringe 50 and second syringe 80 wherein a portion of the solution is extruded in a cycle described herein.

While in a preferred embodiment the continuous extrusion system 100 would utilize single use elements, it is contemplated within the scope of the present invention for larger scale applications the continuous extrusion system 100 could utilize re-usable elements therein that could be cleaned and/or sterilized.

In the preceding detailed description, reference has been made to the accompanying drawings that form a part hereof, and in which are shown by way of illustration specific embodiments in which the invention may be practiced. These embodiments, and certain variants thereof, have been described in sufficient detail to enable those skilled in the art to practice the invention. It is to be understood that other suitable embodiments may be utilized and that logical changes may be made without departing from the spirit or scope of the invention. The description may omit certain information known to those skilled in the art. The preceding detailed description is, therefore, not intended to be limited to the specific forms set forth herein, but on the contrary, it is intended to cover such alternatives, modifications, and equivalents, as can be reasonably included within the spirit and scope of the appended claims.

What is claimed is:

1. An extrusion system configured to provide extrusion of a solution wherein the extrusion system comprises the steps of:
    providing a tubing network, said tubing network having a plurality of tubing lines configured to retain and direct a volume of a solution within said tubing network, said tubing network having an inlet line, said inlet line having a first end and a second end, said second end of inlet line being operably coupled to an inlet valve, said tubing network having a first union, said first union configured to fluidly couple said inlet valve to a purge line, said tubing network further including an exit line;
    connecting said tubing network to an extrusion cartridge, said extrusion cartridge configured to provide extrusion of a solution passing therethrough, said extrusion cartridge having a first port and a second port on opposing sides thereof;
    coupling the inlet line to a solution, wherein the first end of said inlet line is immersed in a solution that requires extrusion;
    connecting said purge line to a waste container;
    placing the exit line into a collection container;
    coupling a first solution movement means, said first solution movement means being operably coupled to said tubing network and said first port of said extrusion cartridge;
    coupling a second solution movement means, said second solution movement means being operably coupled to said tubing network and said second port of said extrusion cartridge;
    drawing at least a portion of the solution into said tubing network;
    purging air from the tubing network and the at least a portion of the solution;
    passing the solution through said extrusion cartridge;
    evacuating the at least a portion of the solution from said tubing network, wherein the at least a portion of the solution is collected in a container.

2. The extrusion system as recited in claim 1, and further including the step of providing a purge line clamp, said purge line clamp operable coupled with said purge line, said purge line clamp having a first position and a second position wherein in the first position the purge line clamp is open and in the second position the purge line clamp is closed inhibiting flow of the solution therethrough.

3. The extrusion system as recited in claim 2, and further including the step of providing an exit line clamp, said exit line clamp operable coupled with said exit line, said exit line clamp having a first position and a second position wherein in the first position the exit line clamp is open and in the second position the exit line clamp is closed inhibiting flow of the solution through outward from said exit line.

4. The extrusion system as recited in claim 3, and further including the step of alternating the position of the first solution movement means and the second solution movement means, wherein during alternating the position of the first solution movement means and the second solution movement means the at least a part of the solution is passed repeatedly through said extrusion cartridge.

5. The extrusion system as recited in claim 2, and further including the step of closing the purge line clamp and the exit line clamp, wherein during the closure of the purge line clamp and the exit line clamp the at least a part of the solution is contained within the tubing network.

6. The extrusion system as recited in claim 1, and further including the step of providing at least a portion of the extrusion system in pre-assembled portions.

7. The extrusion system as recited in claim 3, and further including the step of opening the exit line clamp, wherein ensuing opening of the exit line clamp the at least a portion of the solution can egress from the tubing network for collection thereof.

8. An extrusion system configured to provide extrusion of a solution wherein the extrusion system comprises the steps of:
    providing a tubing network, said tubing network having a plurality of tubing lines configured to retain and direct a volume of a solution within said tubing network, said tubing network having an inlet line, said inlet line having a first end and a second end, said second end of inlet line being operably coupled to an inlet valve, said tubing network having a first union, said first union configured to fluidly couple said inlet valve to a purge line, said tubing network further including an exit line;
    providing a purge line clamp, said purge line clamp operable coupled with said purge line, said purge line clamp having a first position and a second position wherein in the first position the purge line clamp is open and in the second position the purge line clamp is closed;
    providing an exit line clamp, said exit line clamp operable coupled with said exit line, said exit line clamp having a first position and a second position wherein in the first position the exit line clamp is open and in the second position the exit line clamp is closed connecting said tubing network to an extrusion cartridge, said extrusion cartridge configured to provide extrusion of a solution passing therethrough, said extrusion cartridge having a first port and a second port on opposing sides thereof;
    coupling the inlet line to a solution, wherein the first end of said inlet line is immersed in a solution that requires extrusion;
    connecting said purge line to a waste container;
    placing the exit line into a collection container;
    coupling a first syringe, said first syringe being operably coupled to said tubing network and said first port of said extrusion cartridge, said first syringe having a plunger;

coupling a second syringe, said second syringe being operably coupled to said tubing network and said second port of said extrusion cartridge, said second syringe having a plunger;

opening said purge line clamp;

closing said exit line clamp;

drawing at least a portion of the solution into said tubing network, wherein the first syringe includes a plunger and said plunger is moved in an upwards direction so as to facilitate the drawing of the at least a portion of the solution into said tubing network;

purging air from the tubing network and the at least a portion of the solution;

closing the purge line clamp;

passing the solution through said extrusion cartridge;

opening the exit line clamp;

evacuating the at least a portion of the solution from said tubing network, wherein the at least a portion of the solution is collected in a container.

9. The extrusion system as recited in claim 8, and further including the step of alternating the plunger movement of the first syringe and the second syringe, wherein during the alternating the plunger movement of the first syringe and second syringe the at least a portion of the solution is repeatedly passed through said extrusion cartridge.

10. The extrusion system as recited in claim 9, wherein during the step of purging air from the tubing network said purge line clamp is in an open position.

11. The extrusion system as recited in claim 10, wherein said second syringe is operable to egress the at least a portion of the solution from the tubing network through said exit line.

12. The extrusion system as recited in claim 11, wherein the tubing network further includes a second union, said second union operably coupling said second port of said extrusion cartridge, said second syringe and said exit line.

13. The extrusion system as recited in claim 12, wherein the inlet valve is a one-way valve allowing flow of the solution into said tubing network.

* * * * *